(12) United States Patent
Huizinga et al.

(10) Patent No.: US 7,702,469 B2
(45) Date of Patent: Apr. 20, 2010

(54) SYSTEMS AND METHODS FOR PREDICTING AN INDIVIDUAL'S RISK OF DEVELOPING RHEUMATOID ARTHRITIS

(75) Inventors: Tom Willem Johannes Huizinga, Leiden (NL); Anna Helena Maria Van Der Helm-Van Mil, Voorschoten (NL)

(73) Assignee: Academisch Ziekenhuis Leiden H.O.D.N. LUMC, Leiden (NL)

( * ) Notice: Subject to any disclaimer, the term of this patent is extended or adjusted under 35 U.S.C. 154(b) by 400 days.

(21) Appl. No.: 11/697,665

(22) Filed: Apr. 6, 2007

(65) Prior Publication Data

US 2007/0248986 A1 Oct. 25, 2007

Related U.S. Application Data

(60) Provisional application No. 60/790,531, filed on Apr. 10, 2006.

(51) Int. Cl.
*G06F 7/00* (2006.01)
(52) U.S. Cl. .............................. 702/20; 702/19; 703/11; 707/102; 435/7.1; 436/501
(58) Field of Classification Search ............. 702/19–20; 703/13; 707/102; 435/7.1; 436/501
See application file for complete search history.

(56) References Cited

U.S. PATENT DOCUMENTS

2005/0142569 A1* 6/2005 Guild et al. ..................... 435/6

OTHER PUBLICATIONS

Van Der Helm-Van Mil et al., *Antibodies to citrullinated proteins and differences in clinical progression of rheumatoid arthritis*, Arthritis Research & Therapy, vol. 7., R949-R958, (2005).
Hitchon et al., "Early Undifferentiated Arthritis," *Rheumatic Disease Clinics of North America*, vol. 31, No. 4, pp. 605-626, Nov. 2005.
Meyer et al., "Apport de l'Immunologie dans le Diagnostic et la Prise en Charge Therapeutique Precoce de la Polyarthrite Rhumatoide," *Revue Francophone des Laboratoires*, vol. 2006, No. 379, pp. 37-43, Feb. 2006.
Morel et al., "How to predict prognosis in early rheumatoid arthritis," *Best Practice & Research Clinical Rheumatology*, vol. 19, No. 1, pp. 137-146, 2005.
Saleem et al,, "Biomarkers: Strategies to predict outcome of rheumatoid arthritis," *Drug Discovery Today: Therapeutic Strategies*, vol. 3, No. 1, pp. 11-16, Mar. 2006.
Schneider, et al., "Early diagnosis of rheumatoid arthritis," *Zeitschrift Fur Rheumatologie*, vol. 64, No. 8, pp. 516-523, Nov. 2005.
Van Der Helm-Van Mil et al., "A Prediction Rule for Disease Outcome in Patients With Recent-Onset Undifferentiated Arthritis," *Arthritis and Rheumatism*, vol. 56, No. 2, pp. 433-440, Feb. 2007.
Van Der Helm et al., "Genetics and clinical characteristics to predict rheumatoid arthritis: where are we now and what are the future prospects?" *Future Rheumatol.*, vol. 1, No. 1, pp. 79-89, Feb. 2006.
Van Gaalen et al., "Autoantibodies to Cyclic Citrullinated Peptides Predict Progression to Rheumatoid Arthritis in Patients with Undifferentiated Arthritis," *Arthritis and Rheumatism*, vol. 50, No. 3, pp. 709-715, Mar. 2004.
Verpoort et al., "Undifferentiated arthritis—Disease course assessed in several inception cohorts," *Clin. Exp. Rheumatol.*, vol. 22, No. 5, pp. S12-S17, 2004.
Visser, "Early diagnosis of rheumatoid arthritis," *Best Practice & Research Clinical Rheumatology*, vol. 19, No. 1, pp. 55-72, Feb. 2005.
Visser et al., "How to Diagnose Rheumatoid Arthritis Early: A prediction Model for Persistent (Erosive) Arthritis," *Arthritis and Rheumatism*, vol. 46, No. 2, pp. 357-365, Feb. 2002.

* cited by examiner

*Primary Examiner*—Mary K Zeman
(74) *Attorney, Agent, or Firm*—Cooley Godward Kronish LLP

(57) ABSTRACT

Methods for predicting the likelihood of development of rheumatoid arthritis for individuals that present with recent-onset undifferentiated arthritis. The methods are based on the determination of a set of clinical parameter values and determining a predicted risk for developing rheumatoid arthritis by correlating the parameter values with predefined risk values associated with ranges of parameter values. Parameters values that are decisive for the risk for developing rheumatoid arthritis may include serum levels of C-reactive protein, Rheumatoid factors, anti-CCP antibodies, as well as age, gender, localization of the joint complaints, length of morning stiffness, and number of tender and/or swollen joints. The method may be performed by a computer. The invention further relates to a computer, a sample analyser and a computer program product for performing the method and a data carrier with the computer program product.

17 Claims, 5 Drawing Sheets

| | | Risk value |
|---|---|---|
| 1. What is the age? | Multiply with 0.02 | _____ |
| 2. What is the gender? | In case female: 1 point | _____ |

3. How is the distribution of involved joints?

| | | |
|---|---|---|
| In case small joints hands and feet: | 0.5 point | _____ |
| In case symmetric | 0.5 point | _____ |
| In case upper extremities | 1 point | |
| Or: in case upper and lower extremities | 1.5 points | _____ |

4. What is the length of the VAS morning stiffness (range 0-100 mm)?

| | | |
|---|---|---|
| In case 26-90 mm | 1 point | |
| In case > 90 mm | 2 points | _____ |

5. What is the number of tender joints?

| | | |
|---|---|---|
| In case 4-10 | 0.5 point | |
| In case 11 or higher | 1 point | _____ |

6. What is the number of swollen joints?

| | | |
|---|---|---|
| In case 4-10 | 0.5 point | |
| In case 11 or more | 1 point | _____ |

7. What is the C-reactive protein level (mg/L)?

| | | |
|---|---|---|
| In case 5-50 | 0.5 point | |
| In case 51 or higher | 1.5 points | _____ |

| | | | |
|---|---|---|---|
| 8. Is the Rheumatoid factor positive? | If yes | 1 point | _____ |
| 9. Are the anti-CCP antibodies positive? | If yes | 2 points | _____ |

Total risk value _____

SYSTEMS AND METHODS FOR PREDICTING AN INDIVIDUAL'S RISK OF DEVELOPING RHEUMATOID ARTHRITIS

RELATED APPLICATIONS

This application claims priority under 35 U.S.C. 119(e) to U.S. Provisional Application No. 60/790,531, filed Apr. 10, 2006, the entire contents of which are incorporated herein by reference.

FIELD OF THE INVENTION

The present invention relates to a method for predicting the likelihood of development of rheumatoid arthritis in patients with undiagnosed or undifferentiated arthritis. The method may be performed by a computer programmed to differentially diagnose or predict the development of rheumatoid arthritis. The invention further relates to the computer program product and to a data carrier with the computer program product.

BACKGROUND OF THE INVENTION

Individualized treatment decision-making is one of the most important challenges of medicine. To this end several studies have associated clinical variables or gene-expression profile with disease outcome, thereby providing help for clinicians making treatment decisions in several diseases (e.g. Hodgkin's disease, lymphoma).

In the last decade, treatment of rheumatoid arthritis (RA) has evolved to earlier and more aggressive treatment with disease-modifying antirheumatic drugs (DMARDs), as this therapeutic approach prevents joint damage and functional disability.

Patients that present to the outpatient clinic with a recent-onset arthritis are referred to as having early arthritis. Some of these patients may, at first presentation, have a disease that can be classified according to current arthritis evaluation criteria. For example, patients may be directly diagnosed with rheumatoid arthritis or reactive arthritis. Reactive arthritis is an acute form of arthritis which occurs after a viral or bacterial infection that spontaneously disappears in several weeks or months, and which features the following three conditions: (1) inflamed joints; (2) inflammation of the eyes (conjunctivitis); and (3) inflammation of the genital, urinary or gastrointestinal system. However, in rheumatologic practice, many patients present with an early arthritis that cannot be directly classified, and are considered to have an undifferentiated arthritis (UA) which is defined as an early arthritis for which, according to the available classification criteria, no diagnosis can be made.

When patients at first presentation are diagnosed with RA or reactive arthritis, prediction of whether the disease will become persistent or erosive is straightforward, as most RA patients will have a persistent and erosive disease course, while most patients with reactive arthritis will have a self-limiting disease course which in most cases, does not recur.

Several inception cohort studies have shown that about 40-50% of UA patients remit spontaneously, while one third develop RA. Treatment with methotrexate in patients with UA is known to inhibit progression to RA and inhibit joint damage. However, because of the potential toxicity associated with methotrexate and other DMARDs, only patients who have a high risk of developing RA, not those who are likely to remit spontaneously, should be treated with these agents. Thus, a method for predicting which patients with UA are most likely to develop RA would be exceedingly beneficial since only those most likely to develop RA would be exposed to potentially toxic therapeutic agents.

Morel and Combe (2005, Best Practice & Research Clinical Rheumatology 19:137-146) reviewed factors associated with the development of RA, or associated with the development of erosions in patients already diagnosed with the disease. This reference does not disclose a predictive model capable of assessing whether a patient with UA will develop RA.

In addition, several prognostic models that allow prediction of arthritis outcome have been described (e.g. Visser et al., 2002, Arthritis Rheum. 46:357-365; Visser, 2005, Best Practice & Research Clinical Rheumatology 19:55-72). However, the cohorts used to build and validate the models were made up of all early arthritis patients, including those with classified diagnoses (e.g., RA and reactive arthritis), as well as those with UA, with the objective of determining disease progression (erosive disease in particular), rather than differentiating RA from UA. Thus, these models are not capable of assisting in the differential diagnosis of patients that present with UA, and cannot be used to predict development of RA in patients with UA. Thus, there is a need for a method predicting whether patients with UA will develop RA that will address the deficiencies of previous models, as they do not have this predictive ability.

SUMMARY OF THE INVENTION

In a first aspect the present invention relates to a method of predicting whether an individual with undifferentiated arthritis will develop rheumatoid arthritis. Preferably, the method comprises the steps of a) determining for the individual at least one of the following clinical parameter values:
   i) the level of C-reactive protein;
   ii) the presence or absence of Rheumatoid factor; and,
   iii) the presence or absence of anti-CCP antibodies;

b) determining a set of further clinical parameter values comprising at least one of the age of the patient; the gender of the patient; the localization of the joint complaints; the length of the VAS morning stiffness; the number of tender joints; and, determining the number of swollen joints; and, c) predicting the risk of the individual of developing rheumatoid arthritis by correlating the parameter values determined in steps a) and b) with a predefined risk value associated with each particular parameter value.

In step a) of the method at least one of three clinical parameter values, i.e. clinical laboratory test values, are determined. In other embodiments, two of these three values, or all three of these values are determined. The values may be determined in vitro in a sample from the individual, such as from a sample of a body fluid (e.g., blood) or a sample of a blood fraction such as serum or plasma. In other embodiments, the prediction may be made using at least one parameter in group a) and one in group b); at least two parameters in group a) and no parameters in group b); and no parameters in group a) and at least two parameters in group b).

One of the three clinical parameters to be determined is the level of C-reactive protein. Alternatively, levels of high-sensitivity (HS) CRP can be used. Thus, in one embodiment, levels of CRP are determined. In another embodiment, the erythrocyte sedimentation rate (ESR), is used, either instead of, or combined with, determination of CRP levels. In one embodiment, antibodies to CCP are determined; however, antibodies to other CCP variants such as CCP1 or CCP3 may also be used. In addition, determination of anti-CCP antibody titers may be used in place of determination of anti-CCP positivity or negativity is step a) iii) above.

Another clinical parameter to be determined is the presence or absence of Rheumatoid factor (RF) autoantibodies which may be any antibody type, including IgG, IgM and IgA. In one embodiment, Rheumatoid factor antibody positivity is assessed. In another embodiment, Rheumatoid factor antibody titer is determined.

Another clinical parameter to be determined is the presence or absence of antibodies to cyclic-citrullinated peptide (CCP). In one embodiment, antibodies to CCP2 is determined. In another embodiment, antibodies to CCP1 or CCP3 are determined. In one embodiment, anti-CCP antibody positivity is assessed. In another embodiment, anti-CCP antibody titer is determined.

According to one embodiment, step a) comprises providing a sample (e.g., a blood sample) of the individual and determining in vitro at least one of: i) the serum level of C-reactive protein; ii) the presence or absence of Rheumatoid factor; or, iii) the presence or absence of anti-CCP antibodies. In other embodiments, two of these or all three of these are determined. In addition, the alternative determinations described above may also be made (ESR, HS CRP, anti-CCP titers, antibodies to CCP1 or CCP3, other anti-RF) Ig types.

In step b) of the method at least one of further clinical parameter values are determined comprising at least one of the age of the patient; the gender of the patient; the localization of the joint complaints; the length of the VAS morning stiffness; the number of tender joints; and, determining the number of swollen joints. These parameters may be determined by having the patient or healthcare professional answer a questionnaire related to the parameters. The parameters thus need not be determined on the body of the individual. In one embodiment, VAS morning stiffness is rated on a visual analogue scale (0-100). In another embodiment, the severity of morning stiffness is used. A 44-joint count for tender and swollen joint may be performed, scoring each joint on a 0-1 scale. The set of further clinical parameter values determined in step b) may include the age of the patient; the gender of the patient; the localization of the joint complaints; the length of the VAS morning stiffness; the number of tender joints; and the number of swollen joints. In addition, other validated instruments for scoring clinical symptoms of RA or other forms of arthritis can be used, including physician assessment of disease activity, 100 mm VAS, patient's global assessment of health 100 mm VAS, DAS 28, DAS 44, HAQ, HAQ or D1. In one embodiment, a prediction score is calculated as the sum of the risk values for each parameter value. The individual risk values for the clinical parameters are preferably defined as between 50% and 150%, between 75% and 125%, or between 80% and 120% of the values in a)-i):

a) 0 for less than 5 mg/L C-reactive protein;
   0.6 for 5-50 mg/L C-reactive protein;
   1.6 for more than 50 mg/L C-reactive protein;

b) 0 for the absence of the Rheumatoid factor;
   0.8 for the presence of the Rheumatoid factor;

c) 0 for the absence of anti-CCP antibodies;
   2.1 for the presence of anti-CCP antibodies;

d) 0.02 for each year of age;

e) 0 for male gender; 0.8 for female gender;

f) 0.6 in case of involvement of small joints hands and feet;
   0.5 in case of symmetric involvement;
   0.8 in case of involvement of upper extremities; or
   1.3 in case upper and lower extremities;

g) 0 for a length of the VAS morning stiffness less than 26 mm;
   1 for a length of the VAS morning stiffness of 26-90 mm;
   2.2 for a length of more than 90 mm;

h) 0.6 for 4-10 tender joints;
   1.2 for more than 10 tender joints; and, i) 0.4 for 4-10 swollen joints;
   1 for more than 10 swollen joints;

and whereby the maximum prediction score is 14 for an age of 100 years. These parameters represent the regression coefficient, and the parameters directly below are a simplified, rounded version of the above parameters. In addition, a multiplier may be used (e.g., times 100 for each value, or translate a year of age to 12 months of age), which will yield an equivalent scoring system. More preferably, wherein the individual risk values for the clinical parameters are defined as between 75% and 125%, between 80% and 120%, between 90% and 10% of the values in a)-i):

a) 0 for less than 5 mg/L C-reactive protein;
   0.5 for 5-50 mg/L C-reactive protein;
   1.5 for more than 50 mg/L C-reactive protein;

b) 0 for the absence of the Rheumatoid factor;
   1 for the presence of the Rheumatoid factor;

c) 0 for the absence of anti-CCP antibodies;
   2 for the presence of anti-CCP antibodies;

d) 0.02 for each year of age;

e) 0 for male gender; 1 for female gender;

f) 0.5 in case of involvement of small joints hands and feet;
   0.5 in case of symmetric involvement;
   1 in case of involvement of upper extremities; or
   1.5 in case upper and lower extremities;

g) 0 for a length of the VAS morning stiffness less than 26 mm;
   1 for a length of the VAS morning stiffness of 26-90 mm;
   2 for a length of more than 90 mm;

h) 0.5 for 4-10 tender joints;
   1 for more than 10 tender joints; and, i) 0.5 for 4-10 swollen joints;
   1 for more than 10 swollen joints;

and whereby the maximum prediction score is 14 for an age of 100 years.

In the present methods, the risk to develop rheumatoid arthritis may be determined by correlating the prediction score for the individual with the risk associated with that prediction score in accordance with a predetermined probability distribution. In one predetermined probability distribution, a prediction score of about 0 correlates with a risk of about 0.0, a prediction score of about 6-8 correlates with a risk of about 0.5 and a prediction score of about 14 correlates with a risk of about 1.0. An example of one predetermined probability distribution is a probability distribution as depicted in FIG. 5.

In one embodiment, the methods described herein are applied to individuals that present with a recent-onset arthritis, such as recent-onset undifferentiated arthritis. Undifferentiated arthritis (UA) is herein defined as arthritis for which no differential diagnosis can be made using available classification criteria, e.g., the American College of Rheumatology (ACR) 1987 classification criteria for rheumatoid arthritis (see e.g. Arnette et al., 1988, Arthritis Rheum. 31: 315-324).

An individual with recent-onset arthritis is herein defined as an individual with complaints dating from are less than one year, preferably less than 6 months In another aspect, there is provided a method of predicting whether an individual with undifferentiated arthritis will develop rheumatoid arthritis. The method comprises the steps of:

a) reading into a computer a set of at least one of the following clinical parameter values for the individual comprising:
   i) the serum level of C-reactive protein;
   ii) the presence or absence of Rheumatoid factor; and,
   iii) the presence or absence of anti-CCP antibodies;

b) reading into the computer a set of further clinical parameter values for the individual comprising at least one of the age of the patient; the gender of the patient; the localization of the joint complaints; the length of the VAS morning stiffness; the number of tender joints; and, determining the number of swollen joints; and, c) having the computer predict the risk of the individual of developing rheumatoid arthritis;

whereby the computer comprises a processor and memory, the processor being arranged to read from said memory and write into said memory, the memory comprising data and instructions arranged to provide said processor with the capacity to predict the risk of the individual of developing rheumatoid arthritis by correlating the parameter values determined in steps a) and b) with a predefined risk value associated with each particular parameter value as defined herein above.

Another embodiment is a computer for performing a method as herein defined above. Preferably the computer is a computer as depicted in FIG. 1. The computer may comprise a processor and memory, the processor being arranged to read from said memory and write into said memory, the memory comprising data and instructions arranged to provide said processor with the capacity to perform a method of predicting whether an individual with undifferentiated arthritis will develop rheumatoid arthritis, wherein the method comprises at least the steps a), b) and c) as herein described above. In one embodiment, the computer has an input connected to a sample analyser (for analysing body fluid samples, such as e.g. blood samples) for receiving analysis data signals of a sample, and wherein the processor is arranged for determining from said analysis data signals: i) the serum level of C-reactive protein; ii) the presence or absence of Rheumatoid factor; and, iii) the presence or absence of anti-CCP antibodies of said sample as clinical parameters. The processor may be arranged for calculating a prediction score as the sum of the risk values for each parameter value. Alternatively, the processor is arranged for determining the predicted risk for the individual on developing rheumatoid arthritis by correlating the prediction score for the individual with the risk associated with that prediction score in accordance with a predetermined probability distribution as described herein above.

In yet another aspect, there is provided a sample analyser comprising a computer as described herein above. The sample analyser may be an analyser for samples of a body fluid, such as a blood samples or a samples of a blood fraction such as serum or plasma.

In a further aspect, the invention relates to a computer program product comprising data and instructions and arranged to be loaded in a memory of a computer that also comprises a processor, the processor being arranged to read from said memory and write into said memory, the data and instructions being arranged to provide said processor with the capacity to perform a method of predicting whether an individual with undifferentiated arthritis will develop rheumatoid arthritis. The method may comprise at least the steps a), b) and c) as herein described above. In a further aspect the invention relates to a data carrier provided with this computer program product.

In another embodiment, a patient or healthcare professional enters clinical parameters (b), and one or more laboratory values (a) via entry of data through a web portal, and receives a determination of risk of developing rheumatoid arthritis either through the web portal or sent via email, fax or regular mail.

In addition, other clinical parameters such as ESR, HAQ or the presence/absence of erosions may be used in this algorithm, either with or instead of CRP.

BRIEF DESCRIPTION OF THE DRAWINGS

FIG. 4 illustrates and exemplary form that may be used in order to calculate risk values associated with particular parameter values.

DETAILED DESCRIPTION OF THE PREFERRED EMBODIMENTS

Figure 1:
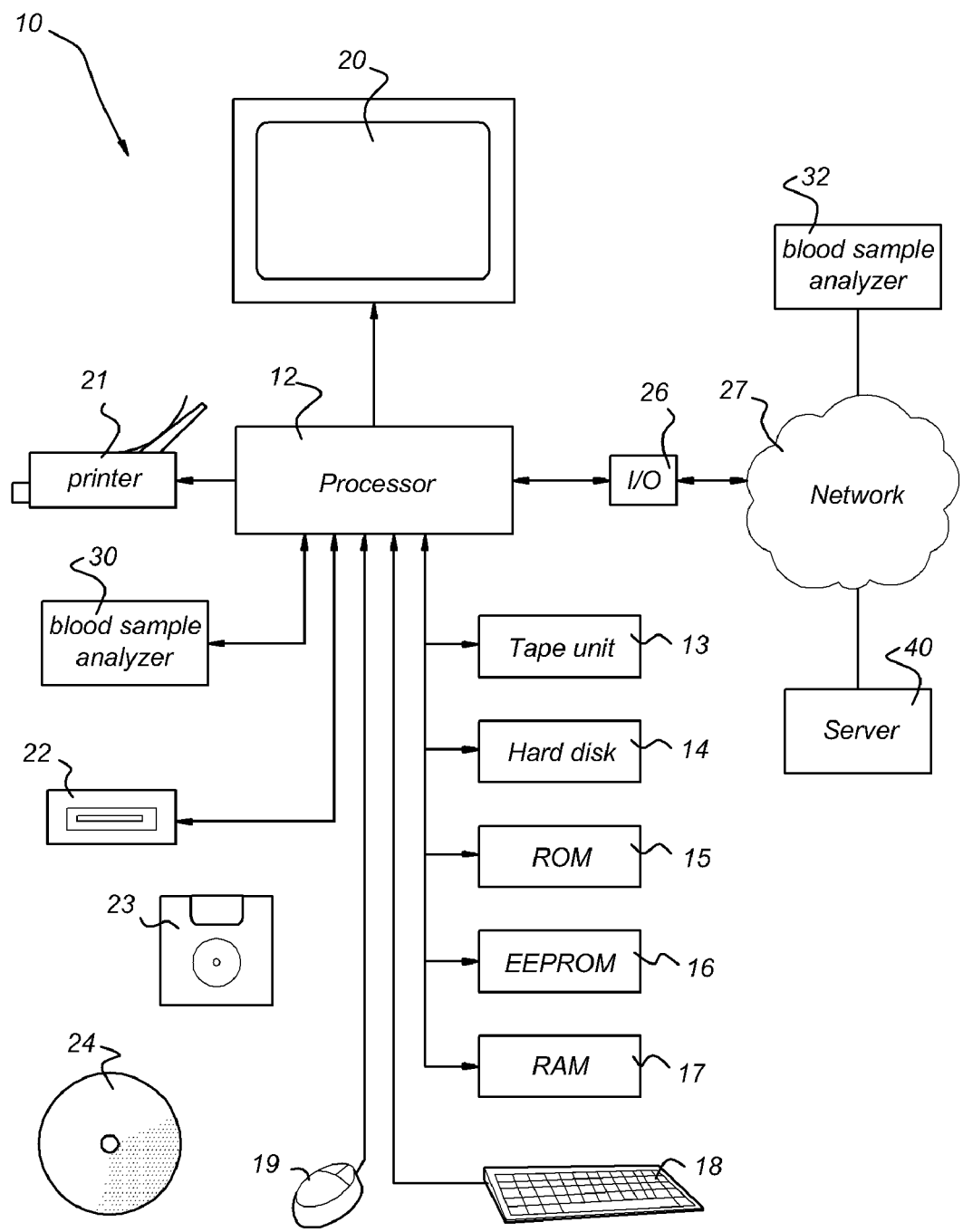
FIG. 1 shows a schematic example of an embodiment of a computer as may be used in one or more of the embodiments described.

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described. In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present.

The methods described herein are directed to predicting whether an individual with undifferentiated arthritis will develop rheumatoid arthritis. One such method comprises the steps of:

a) determining for the individual at least one of the following clinical parameter values:
   i) the level of C-reactive protein (CRP), high-sensitivity C-reactive protein (HS CRP) or erythrocyte sedimentation rate (ESR);
   ii) the presence or absence of Rheumatoid factor autoantibodies or Rheumatoid factor autoantibody titers; and,
   iii) the presence or absence of anti-cyclic citrullinated peptide (CCP) antibodies or anti-CCP antibody titers;

b) determining a set of further clinical parameter values comprising at least one of the age of the patient; the gender of the patient; the localization of the joint complaints; the length of the VAS morning stiffness; the number of tender joints; and, determining the number of swollen joints; and, c) predicting the risk of the individual of developing rheumatoid arthritis by correlating the parameter values determined in steps a) and b) with a predefined risk value associated with each particular parameter value.

In step a) of the method at least one of three clinical parameter values, i.e. clinical laboratory test values, are determined. In other embodiments, two of these three values, or all three of these values are determined. In addition, the predictive method may use at least one parameter from group a) and one parameter from group b); at least two parameters from group a) and none from group b); or none from group a) and at least two from group b). The values may be determined in vitro in a sample from the individual, such as from a sample of a body fluid (e.g., blood) or a sample of a blood fraction such as serum or plasma.

C-reactive protein (CRP) is considered to be a prototypic acute phase reactant, synthesized in the liver as part of a coordinated response by hepatocytes to tissue injury or inflammation. The concentration of CRP increases severalfold in response to different types of tissue damage and inflammation and is considered a significant disease indicator. Various suitable assays for determining the level of CRP are known in the art. High-sensitivity (HS) CRP is used to detect the risk for cardiovascular disease, but the dynamic range of concentrations measured using HS CRP can be found in patients with UA. Thus, in one embodiment, levels of CRP are determined. In another embodiment, the erythrocyte sedimentation rate (ESR), an indicator of inflammation, is used, either instead of, or combined with, determination of CRP levels. These alternate embodiments can also be used in any of the methods disclosed herein.

Another clinical parameter to be determined is the presence or absence of Rheumatoid factor (RF) autoantibodies or RF autoantibody titers. Rheumatoid factor is an autoantibody which is directed against endogenous immunoglobulin, for example IgG Rheumatoid factor are usually antibodies of the IgM class, although other isotypes may also be determined (e.g. IgG, IgA) in any of the methods described herein. In the context of the present disclosure, RF is considered to be present in a sample from an individual upon demonstration of abnormal amount of serum RF by any method for which the result has been positive in less than 5% of normal subjects. Suitable assays for determining the level of RF are known in the art. In one embodiment, Rheumatoid factor antibody positivity is assessed. In another embodiment, Rheumatoid factor antibody titer is determined.

Another clinical parameter to be determined is the presence or absence of antibodies to cyclic-citrullinated peptide (CCP). CCP types include, for example, CCP1, CCP2 and CCP3. In one embodiment, CCP2 is determined. In the context of the present disclosure, antibodies to CCP are considered to be present in a sample from an individual in case of at least 25 arbitrary units in the ELISA, Immunoscan RA Mark 2 (obtainable from Euro-Diagnostica, Arnhem, The Netherlands). Other suitable tests for anti-CCP positivity are described by van Venrooij and van de Putte (2003, Ned Tijdschr Geneeskd. 147(5):191-4). In one embodiment, anti-CCP antibody positivity is assessed. In another embodiment, anti-CCP antibody titer is determined.

According to one embodiment, step a) comprises providing a sample (e.g., a blood sample) of the individual and determining in vitro at least one of the following clinical parameters: i) the serum level of C-reactive protein; ii) the presence or absence of Rheumatoid factor; or iii) the presence or absence of anti-CCP antibodies.

In step b) of the method at least one of further clinical parameter values are determined comprising at least one of the age of the patient; the gender of the patient; the localization of the joint complaints; the length of the VAS morning stiffness; the number of tender joints; and, determining the number of swollen joints. These parameters may be determined by having the patient or healthcare professional answer a questionnaire related to the parameters. The parameters thus need not be determined on the body of the individual. In one embodiment, for determination of the VAS morning stiffness, patients are asked to rate the morning stiffness on a visual analogue scale (0-100) whereby preferably the severity of morning stiffness was used instead of duration of morning stiffness (Hazes et al., 1993 J Rheumatol 20:1138-42; Vliet Vlieland et al., 1997, J Clin Epidemiol 50:757-63). A 44-joint count for tender and swollen joint was performed, scoring each joint on a 0-1 scale (see van Riel et al., 2000, In: "EULAR handbook of clinical assessments in rheumatoid arthritis."; Alphen aan den Rijn, The Netherlands: Van Zuiden Communications; 2000, 10-11). The set of further clinical parameter values determined in step b) may include the age of the patient; the gender of the patient; the localization of the joint complaints; the length of the VAS morning stiffness; the number of tender joints; and the number of swollen joints. In addition, other validated instruments for scoring clinical symptoms of RA or other forms of arthritis can be used, including physician assessment of disease activity, 100 mm VAS, patient's global assessment of health 100 mm VAS, DAS 28, DAS 44, HAQ, HAQ or D1. In one embodiment, a prediction score is calculated as the sum of the risk values for each parameter value. The individual risk values for the clinical parameters are preferably defined as between 50% and 150%, between 75% and 125%, or between 80% and 120% of the values in a)-i):

a) 0 for less than 5 mg/L C-reactive protein;
0.6 for 5-50 mg/L C-reactive protein;
1.6 for more than 50 mg/L C-reactive protein;

b) 0 for the absence of the Rheumatoid factor;
0.8 for the presence of the Rheumatoid factor;

c) 0 for the absence of anti-CCP antibodies;
2.1 for the presence of anti-CCP antibodies;

d) 0.02 for each year of age;

e) 0 for male gender; 0.8 for female gender;

f) 0.6 in case of involvement of small joints hands and feet;
0.5 in case of symmetric involvement;
0.8 in case of involvement of upper extremities; or
1.3 in case upper and lower extremities;

g) 0 for a length of the VAS morning stiffness less than 26 mm;
1 for a length of the VAS morning stiffness of 26-90 mm;
2.2 for a length of more than 90 mm;

h) 0.6 for 4-10 tender joints;
1.2 for more than 10 tender joints; and, i) 0.4 for 4-10 swollen joints;
1 for more than 10 swollen joints;

and whereby the maximum prediction score is 14 for an age of 100 years. These parameters represent the regression coefficient, and the parameters directly below are a simplified, rounded version of the above parameters. In addition, a multiplier may be used (e.g., times 100 for each value, or translate a year of age to 12 months of age), which will yield an equivalent scoring system. It will be appreciated that the specific values presented above may fall within a range of such values. Thus, in certain embodiments, the individual risk values for the clinical parameters are defined as between 75% and 125%, between 80% and 120%, or between 90% and 110% of the values in a)-i):

a) 0 for less than 5 mg/L C-reactive protein;
0.5 for 5-50 mg/L C-reactive protein;
1.5 for more than 50 mg/L C-reactive protein;

b) 0 for the absence of the Rheumatoid factor;
1 for the presence of the Rheumatoid factor;

c) 0 for the absence of anti-CCP antibodies;
2 for the presence of anti-CCP antibodies;

d) 0.02 for each year of age;

e) 0 for male gender; 1 for female gender;

f) 0.5 in case of involvement of small joints hands and feet;
0.5 in case of symmetric involvement;
1 in case of involvement of upper extremities; or
1.5 in case upper and lower extremities;

g) 0 for a length of the VAS morning stiffness less than 26 mm;
1 for a length of the VAS morning stiffness of 26-90 mm;
2 for a length of more than 90 mm;

h) 0.5 for 4-10 tender joints;
1 for more than 10 tender joints; and, i) 0.5 for 4-10 swollen joints;
1 for more than 10 swollen joints;

and whereby the maximum prediction score is 14 for an age of 100 years.

Figures 5, 6:
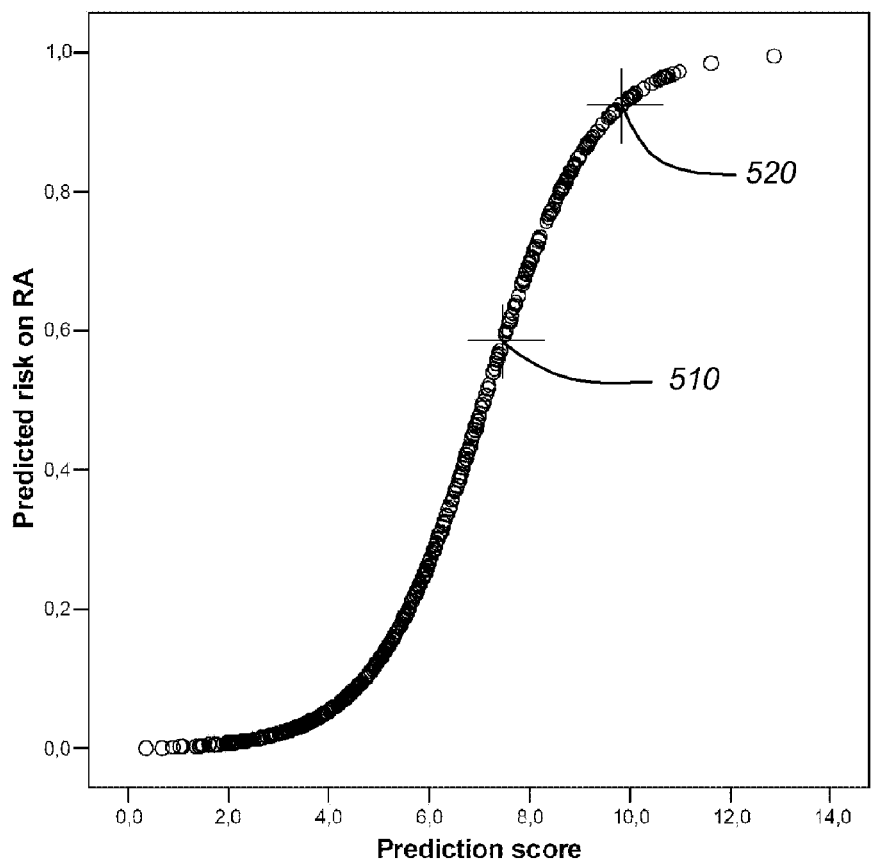
FIG. 5 is a graph illustrating a predicted risk of developing rheumatoid arthritis as a function of the total risk value
FIG. 6 illustrates an exemplary table storing exemplary total risk values associated with predicted risk scores.

In the present methods, the risk to develop rheumatoid arthritis may be determined by correlating the prediction score for the individual with the risk associated with that prediction score in accordance with a predetermined probability distribution. In a preferred predetermined probability distribution a prediction score of about 0 correlates with a risk of about 0.0, a prediction score of about 6-8 correlates with a risk of about 0.5 and a prediction score of about 14 correlates with a risk of about 1.0. An example of a preferred predetermined probability distribution is a probability distribution as depicted in FIG. 5.

In one embodiment, the methods described herein are applied to individuals that present with a recent-onset arthritis, more preferably with recent-onset undifferentiated arthritis.

In another aspect, there is provided a method of predicting whether an individual with undifferentiated arthritis will develop rheumatoid arthritis. The method comprises the steps of a) reading into a computer a set of clinical parameter values for the individual comprising:
i) the serum level of C-reactive protein;
ii) the presence or absence of Rheumatoid factor; and,
iii) the presence or absence of anti-CCP antibodies;

b) reading into the computer a set of further clinical parameter values for the individual comprising at least one of the age of the patient; the gender of the patient; the localization of the joint complaints; the length of the VAS morning stiffness; the number of tender joints; and, determining the number of swollen joints; and, c) having the computer predict the risk of the individual of developing rheumatoid arthritis;

whereby the computer comprises a processor and memory, the processor being arranged to read from said memory and write into said memory, the memory comprising data and instructions arranged to provide said processor with the capacity to predict the risk of the individual of developing rheumatoid arthritis by correlating the parameter values determined in steps a) and b) with a predefined risk value associated with each particular parameter value as defined herein above.

FIG. 1 shows a schematic example of an embodiment of a computer 10 as may be used in one or more of the embodiments described herein. As illustrated in exemplary FIG. 1, the computer 10 comprises a processor 12 for performing arithmetical operations. The processor 12 is connected to memory units that may store instructions and data, such as a tape unit 13, hard disk 14, a Read Only Memory (ROM) 15, Electrically Erasable Programmable Read Only Memory (EEPROM) 16 and a Random Access Memory (RAM) 17. The processor 12 is also connected to one or more input devices, such as a keyboard 18 and a mouse 19, one or more output devices, such as a display 20 and a printer 21, and one or more reading units 22 to read for instance floppy disks 23 or CD ROM's 24. In an embodiment the computer system 10 comprises program lines readable and executable by the processor 12.

The computer 10 shown in FIG. 1 may also comprise an input output device (I/O) 26 arranged to communicate with other computer systems (not shown) via a communication network 27. In the exemplary embodiment of FIG. 1, sample analyser 32 is in data communication with the network 27. In the embodiment of FIG. 1, a local sample analyser 30 is located proximate the computer 10 and a remote sample analyser 32 is positioned remote from the computer 10 and may be in communication with the computer 10 via the network 27. In certain embodiments, any number of sample analysers 30, 32 may be in communication with the computer 10. For example, in one embodiment, the system does not include a local sample analyser 30, but comprises multiple remote sample analysers 32.

In the embodiment of FIG. 1, a server 40 is also in data communication with the network 27. In certain embodiments, the server 40 stores data received from the sample analyser 30,32 and provides this data to the computer 10. In other embodiments, the server 40 and/or the sample analyser 30,32 are configured to perform operations on data determined by the sample analyser 30,32 in order to determine a predicted risk of an individual developing rheumatoid arthritis, such as by using the systems and methods described below. The following description refers to the computer 10 as the device that performs calculations in order to determine a predicted risk of developing rheumatoid arthritis. However, any other computing device, such as the sample analyser 30,32 or the server 40 may also be configured to perform these operations and determine a predicted risk of developing rheumatoid arthritis.

In one embodiment, the computer 10 accesses information and software executing on the server 40 via a graphical user interface, such as a web browser, that is displayed on the display device 20. In this embodiment, the computer 10 provides an interface for viewing, such as by a physician, data from the sample analyser 30 that is stored on the server 40. In one embodiment, the user interface that is displayed on the display device 20 may include data received from the sample analyser 30 via the network 27.

In one embodiment, the computer 10 comprises more and/or other memory units, input devices and read devices than are illustrated in FIG. 1. Moreover, one or more of them may be physically located remote from the processor 12, if required. The exemplary processor 12 is shown as one box, however, it may comprise several processing units functioning in parallel or controlled by one main processor unit that may be located remote from one another, as is known to persons skilled in the art.

It is observed that, although all connections in FIG. 1 are shown as physical connections, one or more of these connections can be made wireless. They are only intended to show that "connected" units are arranged to communicate with one another in some way.

The computer 10 is shown as a computer system, but can be any signal processing system with analog and/or digital and/or software technology arranged to perform the functions discussed here.

The detailed description as given above for the computer 10, may refer to several kind of devices, such as personal computers, servers, laptops, personal digital assistance (PDA), palmtops. All these devices are different kind of computer systems.

The memory units 13, 14, 15, 16, 17 may comprise program lines readable and executable by the processor 12. The programming lines may be such that they provide the computer 10 with the functionality to perform one or more of the methods described below.

As noted above, the computer 10 may be connected to a sample analyser 30, 32 by a communication link. The sample analyser 30, 32 may be arranged to receive a blood sample, or other biological sample, from an individual and perform measurements on this blood sample. The sample analyser 30, 32 may, for instance, be arranged to determine a set of clinical parameter values from the blood sample including:

i) the serum level of C-reactive protein;
ii) the presence or absence of Rheumatoid factor; and/or,
iii) the presence or absence of anti-CCP antibodies.

In the embodiment of FIG. 1, computer 10 is arranged for receiving data-signals relating to measurements of a blood sample from the sample analyser 30, 32 so as to determine clinical parameter values for a set of clinical parameters, such as the parameters i)-iii) noted above. In one embodiment, the connection between the computer 10 and the sample analyser 30 comprises a wired and/or wireless two-way communication link, such as via a direct wired or wireless connection 32 or via the network 27. Alternatively, in case clinical parameter values are determined by different sample analysers, the computer 10 may also comprise multiple connections, each to one of the different sample analysers 30.

The computer 10 may be arranged to read the at least one clinical parameter as determined by the sample analyser 30, 32, and store the at least one clinical parameter in the memory units 13, 14, 15, 16, 17.

The computer 10 may also determine the at least one clinical parameter by reading the at least one clinical parameter from memory 13, 14, 15, 16, 17, or from input devices, such as keyboard 18 and mouse 19, or from one or more reading units 22 to read for instance floppy disks 23 or CD ROM's 24.

The computer 10 may further be arranged to receive a set of further clinical parameter values comprising at least one of the age of the patient; the gender of the patient; the localization of the joint complaints; the length of the VAS morning stiffness; the number of tender joints; and, a number of swollen joints, for example. In other embodiments, fewer or additional further clinical parameters may be received by the computer 10 and used in developing a predicted risk of developing rheumatoid arthritis. In one embodiment, for example, the further clinical parameter values are entered into the computer 10 using one or more input devices, such as a keyboard and/or a mouse, in response to information displayed in a graphical user interface that is displayed on the display device 20. For example, a graphical user interface may be configured to prompt a user to enter each of a plurality of clinical parameter values. In one embodiment, each of the entered clinical parameter values are usable to determine a predicted risk of developing rheumatoid arthritis. In other embodiments, selected clinical parameter values are used in determining a predicted risk of developing rheumatoid arthritis (referred to herein as a "predicted risk"). In one embodiment, a confidence level in the predicted risk increases as the number of clinical parameter values that are entered into the graphical user interface, and are processed by the computer 10, increases. Thus, while a predicted risk may be determined based on as few as two clinical parameter values, the confidence level of the predicted risk may increase as additional clinical parameter values are received and considered in developing the predicted risk.

In one embodiment, the computer 10 may be arranged to read these further parameter values from memory 13, 14, 15, 16, 17, from input devices, such as keyboard 18 and mouse 19, or from one or more reading units 22 to read for instance floppy disks 23 or CD ROM's 24.

As noted above, the computer 10 may be arranged to determine a predicted risk of the individual developing rheumatoid arthritis by correlating at least two of the clinical parameter values with a predefined risk value associated with each particular parameter value. The predicted risk score may be outputted by the computer 10 using one or more output devices, such as display 20 and printer 21. Also, computer 10 may be arranged for transmission of the predicted risk value over the network 27 to another computer system (not shown).

In one embodiment the predicted risk is transmitted to a remote computing system and displayed to a user via a graphical user interface. In another embodiment, the predicted risk is transmitted via e-mail to the individual, a physician, and/or another computing system. In yet another embodiment, the predicted risk may be transmitted via facsimile or printed and delivered to the individual and/or physician. In certain embodiments, the risk values associated with each of the clinical parameter values and the total risk value for the individual are also transmitted from the computer 10 to another computing device. In one embodiment, the predicated risk is stored on the server 40 and is accessible to users with proper authorization to view the predicted risk, such as the individual and the individual's healthcare providers.

Figure 2:
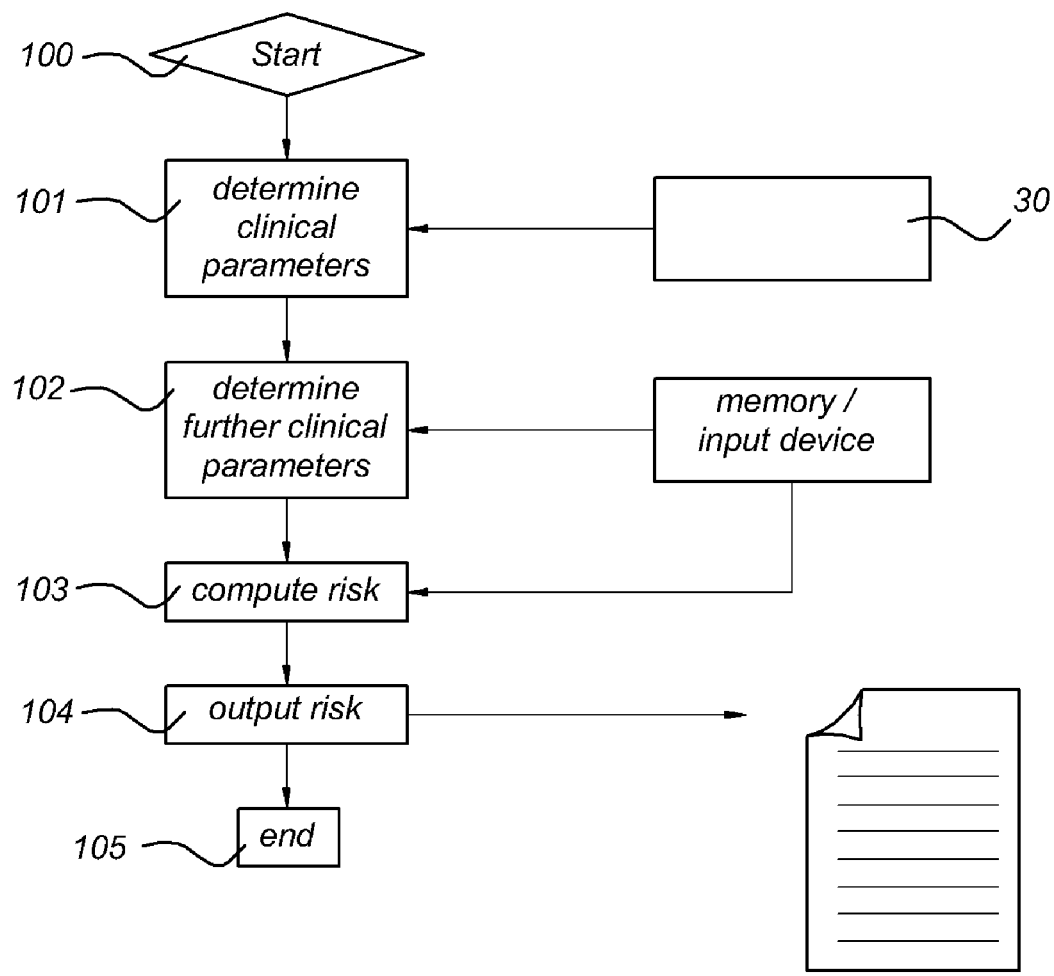
FIG. 2 schematically depicts a flow diagram of a procedure as may be executed by the computer of FIG. 1 according to an embodiment of the invention.

FIG. 2 schematically depicts a flow diagram of a procedure as may be executed by computer 10, or other computing device, according to an embodiment of the invention. Depending on the embodiment, certain of the actions described below may be removed, others may be added, and the sequence of actions may be altered.

In a first action 100, the computer 10 starts executing the procedure. This action may for instance be triggered by input from a user into a graphical user interface displayed on the display device 20.

In a next action 101, the computer 10 determines at least one clinical parameter using sample analyser 30, 32. This action may comprise the steps of 101a) the processor 12 requesting the sample analyser 30, 32 to output data-signals relating to the measured values of a blood sample to the processor 12; 101b) the processor 12 receiving the data-signals, and 101c) the processor 12 (optionally) storing the data-signals relating to the measured values in memory 13, 14, 15, 16, 17. In an advantageous embodiment, the data-signals that are received from the sample analyser 30, 32, comprise parameter values associated with each of one or more clinical parameters, such as, for example, a parameter value indicating a serum level of C-reactive protein in the blood sample and a parameter value indicating presence or absence of Rheumatoid factor in the blood sample. In one embodiment, action 101a) may also comprise that the processor 12 requests the sample analyser 30, 32 to perform certain measurements on the blood sample relating to determining a set of clinical parameter values, such as clinical parameters values for clinical parameters i)-iii) discussed above before transmitting the data-signals.

In a next action 102, the processor 12 determines at least one of the further clinical parameter values using one or more input devices as described above, or alternatively, from associated data already stored in memory 13, 14, 15, 16, 17. As noted above, the further clinical parameter values may be entered into a computing device, such as computer 10, via a graphical user interface. In one embodiment, the further clinical parameter values are entered into the computer 10 by a caregiver in response to comments from the individual. In another embodiment, a user interface is accessible to the individual via a computer in communication with the network, so that the individual may enter the further clinical parameter values for use in this method.

In a further action 103, the computer 10 determines a predicted risk of an individual developing rheumatoid arthritis by correlating each of at least two of the clinical parameter values and further clinical parameter values determined in action 101 and 102 above with predefined risk values that are associated with each particular parameter value. These risk values may then be combined in order to determine a total risk value for the individual. Finally, the total risk value may be associated with a predicted risk of the individual developing rheumatoid arthritis. In one embodiment, ranges of values for each of the clinical parameter values are associated with particular risk values. In another embodiment, risk values for particular clinical parameters are determined according to formulas specific to each clinical parameter. In one embodiment, the total risk value is the sum of each of the risk values that have been associated with the clinical parameter values. In other embodiments, the total risk value may be calculated using only a portion of the risk values.

In one embodiment, ranges of total risk values are each associated with a predicted risk that the individual will develop rheumatoid arthritis. The number of ranges of total risk values and the granularity of the predicted risks associated with the ranges may very depending on the application. For example, in one embodiment only two ranges of total risk values are used, where total risk values that are within a first range are associated with predicted risks indicating that an individual is likely to develop rheumatoid arthritis, and total risk values that are within a second range are associated with predicted risks indicating that the individual is not likely to develop rheumatoid arthritis. In another embodiment, total risk values are associated with one of three predicted risks, such as low, moderate, and high risks of developing rheumatoid arthritis. In other embodiments, total risk values are each associated with one of a plurality, such as 5, 10, 15, or 20, for example, of different predicted risk scores. In one embodiment, the predicted risk scores are expressed as a percentage chance that the individual will develop rheumatoid arthritis. In one embodiment, the predicted risk is determined based on a formula in which the total risk value is a factor. In this embodiment, ranges of total risk values may not be necessary as each total risk value may result in a different predicted risk.

In one embodiment, the predefined risk values associated with parameter values, or ranges of parameter values, may be stored in memory 13, 14, 15, 16, 17 and retrieved from memory 13, 14, 15, 16, 17 by the processor 12 or may be received using input devices as described above.

In a next action 104, the computer 10 outputs the computed predicted risk of an individual of developing rheumatoid arthritis by using one or more output devices, such as display 20 and printer 21 or by transmission of the computed predicted risk to another computer system (not shown), such as via email or storage of the predicted risk on a server that is accessible to other users. Also, the computer 10 may store the computed predicted risk, and/or the risk values and total risk values, in memory 13, 14, 15, 16, 17 or on the server 40.

In action 105, the execution of procedure ends. If needed, the procedure may be resumed at action 101 to execute once more.

According to a further embodiment, the sample analyser 30, 32 and/or the server 40 comprises a computer, having the components such as those described above with reference to computer 10, that is configured to perform the procedure described in FIG. 2. Thus, in one embodiment the sample analyser 30, 32 and/or server 40 are capable of computing a predicted risk score of the individual developing rheumatoid arthritis by correlating at least two of the clinical parameter values determined above with a predefined risk value associated with each particular parameter value.

Figure 3:
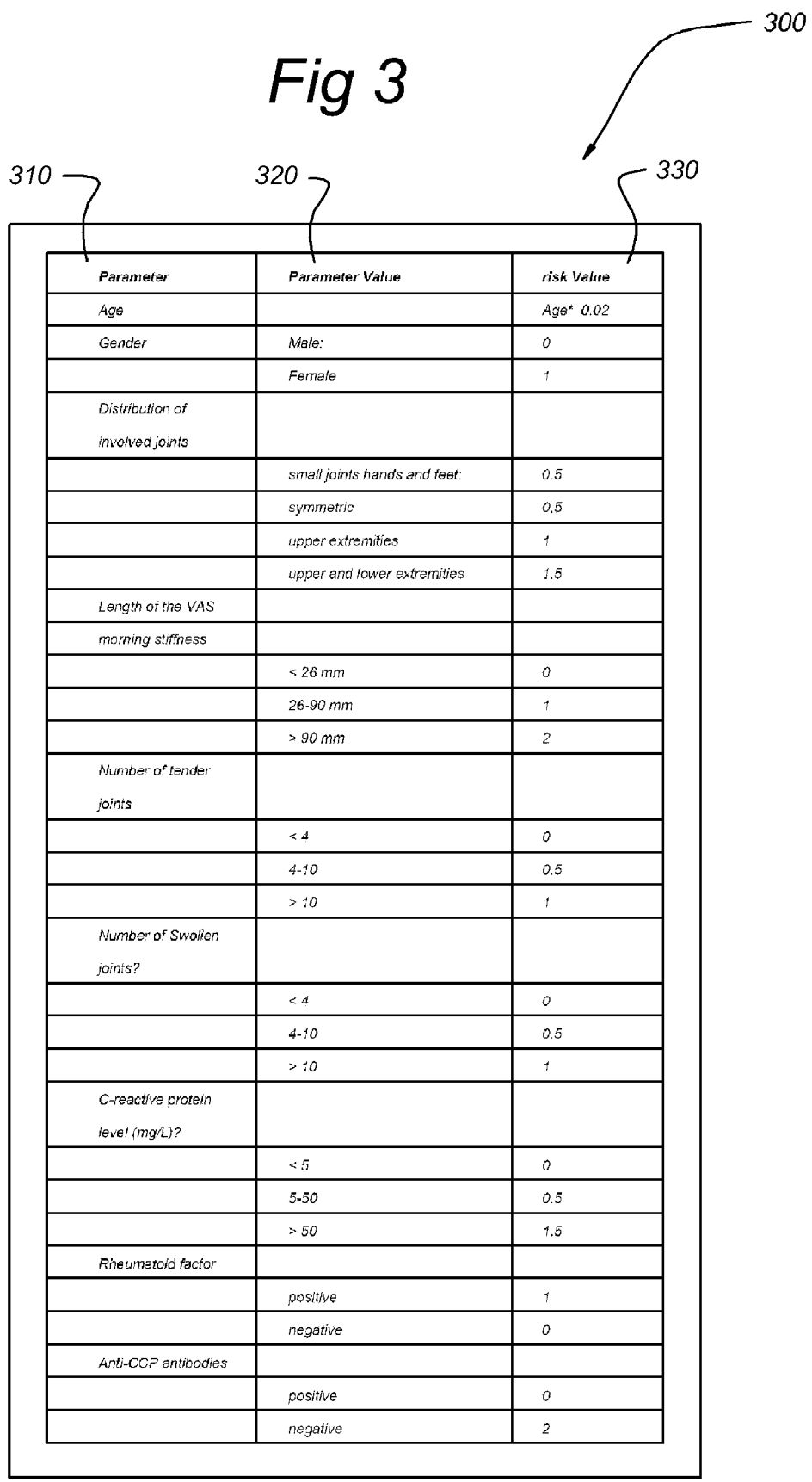
FIG. 3 illustrates an exemplary table storing exemplary risk values that are associated with ranges of parameter values for several clinical parameters.

FIG. 3 is a table 300 illustrating exemplary risk values that are associated with ranges of parameter values for several clinical parameters. In the embodiment of FIG. 3, risk values are associated with each of nine clinical parameters. In other embodiments, fewer or more clinical parameters may be associated with risk values. The table 300 may advantageously be stored in a memory device and accessed by the computer 10 in order to determine risk values for any of the listed parameters. The table 300 may be stored in a memory of the computer 10, at the server 40, or at the sample analyser 30, 32. In another embodiment, the table 300 is converted to a worksheet format, such as will be discussed below with reference to FIG. 4, that may be printed or viewed in a graphical user interface.

In the embodiment of FIG. 3, a first column 310 lists clinical parameters, a second column 320 lists possible parameter values associated with each of the clinical parameters, and a third column 330 lists a risk value that is associated with respective ranges of parameter values. In one embodiment, each of the risk values assigned to an individual are summed in order to determine a total risk value that will be associated with a predicted risk of the individual developing rheumatoid arthritis. Below are exemplary parameter values for two individuals, individual A and individual B, and the associated risk values assigned to the individuals using the table 300.

| Risk Values and Total Risk Value for Individual A | | |
|---|---|---|
| Parameter | Parameter Value | Assigned Risk Value |
| Age | 50 | 1 (i.e., 50* .02) |
| Gender | Male | 0 |
| Distribution of involved joints | Upper and lower extremities | 1.5 |
| Length of VAS morning stiffness | 56 mm | 1 |
| Number of tender joints | 12 | 1 |
| Number of swollen joints | 7 | .5 |
| C-reactive protein level | 12 | .5 |

-continued

Risk Values and Total Risk Value for Individual A

| Parameter | Parameter Value | Assigned Risk Value |
|---|---|---|
| Rheumatoid factor | Negative | 0 |
| Anti-CCP antibodies | Negative | 2 |
| Total Risk Value | | 7.5 |

Risk Values and Total Risk Value for Individual B

| Parameter | Parameter Value | Assigned Risk Value |
|---|---|---|
| Age | 75 | 1.5 (i.e., 75* .02) |
| Gender | Female | 1 |
| Distribution of involved joints | Symmetric | .5 |
| Length of VAS morning stiffness | 85 | 1 |
| Number of tender joints | 12 | 1 |
| Number of swollen joints | 10 | .5 |
| C-reactive protein level | 52 | 1.5 |
| Rheumatoid factor | Positive | 1 |
| Anti-CCP antibodies | Negative | 2 |
| Total Risk Value | | 10 |

As indicated above, the total risk value for individual A is 7.5, while the total risk value for individual B is 10. In one embodiment, a higher total risk value indicates a higher risk of developing rheumatoid arthritis. Thus, in this embodiment, individual B is more likely to develop rheumatoid arthritis than individual A. In other embodiments, however, lower total risk scores may indicate lower risks of developing rheumatoid arthritis.

As described in further detail below, these total risk values may now each be associated with a corresponding predicted risk of the individual developing rheumatoid arthritis. In one embodiment, each of the parameter values for the individuals are entered into a computing device, such as the computer 10 via a graphical user interface, and the computing device determines the risk values associated with each of the parameter values such as by accessing table 300 stored in a memory. In the embodiment described below with respect to FIG. 4, a user manually selects the risk values associated with particular parameter values and calculates a total risk value.

FIG. 4 illustrates an exemplary checklist 400 that may be used to record clinical parameter values and associate risk values with each of the clinical parameter values. In the embodiment of FIG. 4, a user, such as a physician, records information regarding the patient on the checklist 300, and assigns risk values to each of the parameter values associated with the particular parameter value. In the embodiments of FIGS. 3 and 4, specific parameters, as well as specific risk values associated with each of the parameters are used in determining the total risk value for the individual. However, in other embodiments fewer or more parameters may be used in order to determine a total risk value. Additionally, the risk values associated with parameter values may be higher or lower depending on the specific implementation. For example, in an embodiment that uses only a portion of the parameters listed in FIG. 3, the risk values associated with certain parameter values may be adjusted.

FIG. 5 is a graph illustrating a predicted risk of developing rheumatoid arthritis as a function of the total risk value. In the embodiment of FIG. 5, the vertical axis represents a predicted risk of an individual developing rheumatoid arthritis, while the horizontal axis represents an individual's total risk value. Thus, a total risk value may be associated with a predicted risk using the graph of FIG. 5. For example, with regard to individual A discussed above with reference to FIG. 3, a total risk value of 7.5 was calculated. Using the graph of FIG. 5, individual A may be assigned a predicted risk of about 60% (see intersection at about point 510). In one embodiment, a risk score of 60% indicates that the individual has a 60% chance of developing rheumatoid arthritis. Using the graph of FIG. 5 again, individual B was assigned a total risk value of 10, which corresponds with a predicted risk of about 90% (see intersection at about point 520). Thus, in this embodiment individual B has about a 90% risk of developing rheumatoid arthritis.

In one embodiment, predicted risk data, such as the data illustrated in FIG. 5, may be expressed as an algorithm that converts a total risk value to a predicted risk. In this embodiment, once a total risk value is determined, the algorithm may automatically convert the total risk value to a percentage predicted risk that the individual develops rheumatoid arthritis. In one embodiment, the algorithm calculates the predicted risk after each of the parameter values are entered into, or received by, the computer 10. In another embodiment, the computer 10 is configured to execute an algorithm to determine a predicted risk score after entry of each parameter value. Accordingly, a physician or user entering parameter values may watch the predicted risk change as additional parameter values are entered into the computer 10.

FIG. 6 illustrates a table 600 storing exemplary total risk values associated with predicted risk scores. In the embodiment of FIG. 6, a total risk value of less than four is associated with a predicted risk score of "low", indicating that the individual has a low predicted risk of developing rheumatoid arthritis. In this embodiment, a total risk value of greater than 10 is associated with a predicted risk score of "high", while total risk values in the range of 4-10 are associated with a predicted risk or of "moderate."

The predicted risk scores illustrated are exemplary, and are not intended to limit the scope of predicted risk scores that may be used in conjunction with the systems and methods described herein. For example, in certain embodiments, the predicted risk scores may be numerical, such as percentages. In other embodiments, the predicted risk scores may be analogous to grades, such as giving the individual a grade from A-F, where A indicates a very low risk of developing rheumatoid arthritis and F indicates a very high risk of developing rheumatoid arthritis. In other embodiments any other type of predicted risk score may be associated with a total risk value and provided to an individual.

Following is a discussion of the development of specific models for associating parameter values with risk values and associating total risk scores with appropriate predicted risk scores. The following clinical test data is provided as exemplary of methods for generating such models, and is not intended as limitive of other methodologies that may be used to develop similar models, or of the parameters, risk values, or predicted risk scores that may be used in a model.

In one embodiment, a predicted risk score model was derived using the Leiden Early Arthritis Clinic, an inception cohort containing more than 1900 patients with recent-onset arthritis of whom about 1700 have completed at least one-year follow-up. This cohort started in 1993 at the department of Rheumatology of the Leiden University Medical Center, the only referral center for rheumatology in a health care region of ~400,000 inhabitants in the Netherlands. General practitioners were encouraged to refer patients directly when arthritis was suspected; patients were included if physical examination revealed arthritis. At first visit various variables were collected. The rheumatologist answered a questionnaire inquiring about the initial symptoms as reported by the patient: type, localization and distribution of initial joint symptoms, symptom duration and course of start complaints. The smoking and family history were assessed. Patients rated the morning stiffness on a visual analogue scale (0-100). For the present study, severity of morning stiffness was used instead of duration of morning stiffness as the first may be a better discriminator. The Health Assessment Questionnaire (HAQ) yielded an index of disability. A 44-joint count for tender and swollen joint was performed, scoring each joint on a 0-1 scale. Compression pain of metacarpophalangeal and metatalohalangeal joints was recorded. Baseline blood samples were taken for determination of ESR, C-Reactive protein (CRP), IgM rheumatoid factor (RF, ELISA), and antibodies to cyclic-citrullinated peptide 2 (CCP; ELISA, Immunoscan RA Mark 2, Euro-Diagnostica, Arnhem, The Netherlands). The cut-off level for anti-CCP positivity was 25 arbitrary units. Radiographs of hands and feet were made and scored according to Sharp-van der Heijde.

570 patients were determined to have an arthritis that could not be classified according to the ACR-criteria and were documented as undifferentiated arthritis (UA). After 1-year follow-up, the disease status of all UA-patients was examined to determine whether they had developed RA or other diagnosis according to the ACR-criteria. Inherent to the design of an inception cohort, the duration of follow-up differed within the study population and at the moment of analysis (July 2005). The majority of UA-patients (94%) had been followed for more than one year (mean follow-up 8 years, SD 3 years).

Patients included in the placebo-arm of this trial, a double-blind placebo-controlled randomized trial in which patients with recent-onset UA were treated with either methotrexate or placebo, were used for validation (n=55). Exclusion of the UA-patients that were also included in the EAC cohort resulted in 36 independent UA-patients. Two of these were lost to follow-up. For each patient the progression score at baseline was calculated and the development of RA after 1-year follow-up was assessed.

The UA-patients that did or did not develop RA were compared using the Chi-square test for nominal variables and the student's t-test for continuous variables. Symptom duration was categorized. Subsequently all clinical variables were entered as possible explanatory variables in a logistic regression analysis with the disease outcome (RA or non-RA) at one-year follow-up as the dependent variable. Using a backward selection procedure, the most significant independent variables were identified, using $p>0.10$ as the removal criteria. In the logistic regression model the predicted probability of RA is related to the covariates via the predictive index: $B1*x1+B2*x2+B3*x3 \ldots Bk*xk$. The B (regression coefficient) of the covariate indicates an estimate of the relative magnitude of the prognostic power of the concerning variable. Using the predictive index, for every subject the predicted probability of RA development was calculated. For continuous variables (age, VAS-score, tender and swollen joint count, CRP) the effect was studied both as continuous variables and as categorized. Categories were pooled if corresponding regression coefficients were similar. Data on VAS morning stiffness were missing in 160 subjects, data on anti-CCP antibodies in 64 subjects and data on disease duration in 22 subjects. To prevent exclusion of these subjects from the logistic regression analysis, the median value was imputed. The multivariate regression analysis was performed using 562 UA patients, because for 8 patients one or more of the following variables were missing: rheumatoid factor (n=1), CRP (n=1), tender joint count (n=5), swollen joint count (n=4).

To get a simplified prediction rule, the regression coefficients of the predictive variables were rounded to the nearest number ending in 0.5 or 0.0 resulting in a weighted score; subsequently the independent predictive variables were summed. The calculated total risk values were compared with the observed percentage progression to RA. The positive and negative predictive values were determined for several cut-off values of the total risk values. To evaluate the diagnostic performance, a receiver-operating characteristic (ROC) curve was constructed. The area under the ROC curve (AUC) provided a measure of the overall discriminative ability of a model. For internal validation, cross-validation was performed to control for over-fitting. Cross-validation mimics the prediction situation and yields for each observation a total risk value based on the other (n−1) observations. To validate the model a ROC-curve was made using the cross-validated predictions as well as the external validation cohort.

Of 570 UA-patients, 177 developed RA during the first year of follow-up, 94 patients developed other rheumatologic diseases, 149 patients remained unclassified and 150 patients achieved clinical remission defined as discharge from the outpatient clinic because of absence of arthritis without DMARDs. For further analysis, the patients with other rheumatologic diagnoses, unclassified arthritis and remission were assembled as the non-RA group (n=393).

Characteristics of UA-patients that did and did not develop RA are compared in Table 1. In univariate analysis, all variables except smoking were significantly associated with progression to RA.

TABLE 1

Characteristics at inclusion of UA-patient that did not and did progress to RA.

| Patient characteristic | Non-RA N = 393 | RA N = 177 | P |
|---|---|---|---|
| Age, mean ± SD | 48.6 ± 17.0 | 56.3 ± 15.3 | <0.001 |
| Female, n (%) | 208 (53) | 121 (68) | 0.001 |
| Positive family history for RA, n (%) | 81 (21) | 54 (31) | 0.01 |
| Course of initial symptoms, n (%) | | | |
| acute <24 hr | 116 (30) | 36 (20) | |
| subacute >24 hr | 123 (31) | 51 (29) | |
| gradual | 141 (36) | 86 (49) | |
| intermittent | 13 (3) | 4 (2) | 0.02 |
| Symptom duration at inclusion, n (%) | | | |
| <6 weeks | 103 (27) | 18 (11) | |
| 6 weeks-3 months | 80 (21) | 43 (25) | |
| 3-6 months | 89 (23) | 47 (28) | |
| >6 months | 107 (28) | 61 (36) | <0.001 |
| Localisation affected joints, n (%) | | | |
| small hand/feet | 171 (44) | 95 (54) | |
| big joints | 165 (42) | 32 (18) | |
| both | 57 (15) | 50 (28) | <0.001 |
| Localisation affected joints, n (%) | | | |
| Symmetric | 147 (37) | 118 (67) | <0.001 |
| Localisation affected joints, n (%) | | | |
| upper extremities | 177 (45) | 71 (40) | |
| lower extremities | 139 (35) | 22 (12) | |
| both | 77 (20) | 84 (47) | <0.001 |

TABLE 1-continued

Characteristics at inclusion of UA-patient that did not and did progress to RA.

| Patient characteristic | Non-RA N = 393 | RA N = 177 | P |
|---|---|---|---|
| Morning stiffness (VAS), mean ± SD | 35.5 ± 30.0 | 53.3 ± 30.1 | <0.001 |
| Compression pain MCP joints, n (%) | 159 (40) | 116 (66) | <0.001 |
| Compression pain MTP joints, n (%) | 134 (34) | 103 (58) | <0.001 |
| Number tender joints, median (IQR) | 5 (2-11) | 11 (7-22) | <0.001 |
| Number swollen joints, median (IQR) | 2 (1-4) | 4 (2-7) | <0.001 |
| CRP level (mg/L), median (IQR) | 8 (3-21) | 14 (7-43) | <0.001 |
| ESR level (mm1$^{st}$ hr), median (IQR) | 17 (8-38) | 32 (19-53) | <0.001 |
| Rheumatoid factor positive, n (%) | 56 (14) | 84 (47) | <0.001 |
| Anti-CCP positive, n (%) | 38 (11) | 83 (51) | <0.001 |
| HAQ score, mean ± SD | 0.7 ± 0.6 | 1.0 ± 0.7 | <0.001 |
| Smoking, n (%) | 187 (48) | 84 (47) | 1.0 |

In a logistic regression, analysis of the independent predictive variables for RA development were: age, gender, localization of joint complaints (small/big joints, symmetric/asymmetric, upper/lower extremities), morning stiffness, tender and swollen joint count, CRP-level, RF and anti-CCP antibodies (Table 2). The resulting model had a fraction of explained variation (Nagelkerke $R^2$) of 0.57 and, when taking a predicted probability of 0.5 as cut off value, predicted 83% of patients correctly. The coefficients for the simplified total risk value are listed in Table 2. Thus, in one embodiment, the computing device determines total risk values for an individual using the coefficients indicated in Table 2.

As noted above with reference to FIG. 4, a worksheet may be used to calculate a total risk value from multiple risk values. In the embodiment of FIG. 4, the total risk value ranges between 0 and 14; a higher score indicates a higher risk to develop RA. For every UA patient the total risk value was calculated. In this particular study, all UA patients with a total risk value ≦3 did not progress to RA during the one-year follow-up, and all UA patients with a score ≧11 had progressed to RA during that same period. The patients with intermediate scores (4-10) had progressed to RA in increasing frequency at rising scores. Table 3, below, shows the percentage of the patients that progressed to RA for several cut-off values of the total risk value. For example if the scores 5.0 and 9.0 were chosen as cut-off values, 97% of UA patients with a score a score ≦5.0 did not develop RA and a score ≧9.0 was associated with progression to RA in 84% of patients. If the cut-off values were 6.0 and 8.0, 91% of UA patients with a score ≦6.0 did not develop RA (negative predictive value 91%) and a score ≧8.0 corresponded with progression to RA in 84% (positive predictive value 84%). With these cut-off values 145 UA patients (25%) had a score between 6.0 and 8.0, indicating that for these patients no adequate prediction could be made. Twenty-five UA patients did not fulfill the 1987 ACR criteria for RA after one-year follow-up, but developed RA later in the disease course. These patients had a median total risk value of 5.7 (IQR 4.8-6.2); this value is in between the scores of the UA patients that did and did not develop RA during the first year of follow-up (median score 7.7, IQR 6.6-8.8 and median score 4.6, IQR 3.3-5.9 respectively).

TABLE 2

Independent predictive variables for RA development resulting from multivariate regression analysis

| Variable | B * | OR | P | Points # |
|---|---|---|---|---|
| Gender | 0.8 | 2.1 | 0.003 | 1 |
| Age | 0.02 | 1.02 | 0.011 | 0.02/year |
| Localisation small joints hand/feet | 0.6 | 1.8 | 0.024 | 0.5 |
| Localisation symmetric | 0.5 | 1.6 | 0.075 | 0.5 |
| Localisation upper extremities | 0.8 | 2.1 | 0.04 | 1 |
| upper and lower extremities | 1.3 | 3.5 | 0.001 | 1.5 |
| VAS morning stiffness | | | | |
| 0-25 | — | — | — | — |
| 26-50 | 0.9 | 2.3 | 0.009 | 1 |
| 51-90 | 1.0 | 2.7 | 0.006 | 1 |
| >90 | 2.2 | 9.3 | <0.001 | 2 |
| Number tender joints | | | | |
| 0-3 | — | — | — | — |
| 4-10 | 0.6 | 1.8 | 0.082 | 0.5 |
| >10 | 1.2 | 3.3 | 0.003 | 1 |
| Number swollen joints | | | | |
| 0-3 | — | — | — | — |
| 4-10 | 0.4 | 1.5 | 0.18 | 0.5 |
| >10 | 1.0 | 2.8 | 0.038 | 1 |
| CRP level | | | | |
| 0-4 | — | — | — | — |
| 5-50 | 0.6 | 1.6 | 0.13 | 0.5 |
| >50 | 1.6 | 5.0 | 0.00 | 1.5 |
| RF positive | 0.8 | 2.3 | 0.009 | 1 |
| Anti-CCP positive | 2.1 | 8.1 | <0.001 | 2 |

* B means regression coefficient
Points for the simplified prediction rule derived from the regression coefficient

TABLE 3

Total risk value and number (%) of patients that did not or did progress to RA, as well as several cut-off values for total risk values with corresponding chances on RA development

| Score* | Non-RA n (%) | RA n (%) |
|---|---|---|
| 0 | 1 (100) | 0 (0) |
| 1 | 8 (100) | 0 (0) |
| 2 | 42 (100) | 0 (0) |
| 3 | 58 (100) | 0 (0) |
| 4 | 78 (93) | 6 (7) |
| 5 | 73 (85) | 13 (15) |
| 6 | 63 (74) | 22 (26) |
| 7 | 37 (49) | 38 (51) |
| 8 | 16 (33) | 33 (67) |
| 9 | 6 (14) | 36 (86) |
| 10 | 5 (23) | 17 (77) |
| 11 | 0 (0) | 8 (100) |
| 12 | 0 (0) | 1 (100) |
| 13 | 0 (0) | 1 (100) |
| 14 | 0 | 0 |
| Total | 387 | 175 |
| Score ≦4.0 | 145 (99) | 1 (1) |
| 4.0-10.0 | 240 (60) | 159 (40) |
| ≧10.0 | 2 (12) | 15 (88) |
| Score ≦5.0 | 223 (97) | 8 (3) |
| 5.0-9.0 | 157 (55) | 131 (46) |
| ≧9.0 | 7 (16) | 36 (84) |
| Score ≦6.0 | 296 (91) | 28 (9) |

TABLE 3-continued

Total risk value and number (%) of patients that did not or did progress to RA, as well as several cut-off values for total risk values with corresponding chances on RA development

| Score* | Non-RA n (%) | RA n (%) |
|---|---|---|
| 6.0-8.0 | 76 (52) | 69 (48) |
| ≧8.0 | 15 (16) | 78 (84) |

* Total risk values were rounded to the nearest number ending in .5 or .0. (i.e. scores ≦0.5 are in the category 0, >0.5 and ≦1.5 in the category 1, etc)

The discriminative ability of the logistic regression model and the prediction rule were evaluated with a ROC curve. Both had an AUC of 0.89 (SE 0.014). The finding that the AUC of the logistic regression model and the prediction rule were equal, indicates that the derivation of the prediction rule from the logistic regression model had not introduced a loss in discriminative ability.

Cross-validation was used to control for over-fitting. This procedure yielded for every patient a predicted probability of RA, based on the model developed using another patient cohort. The AUC of the cross-validated predictions nearly equalled the AUC of the total risk value: 0.87 (SE 0.015), indicating that over-fitting is not a major problem.

In the validation cohort, 47% of UA patients had progressed to RA after one-year follow-up. The UA patients who had progressed to RA had a median total risk value of 8.0 (IQR 6.1-9.1) and the patients who did not develop RA had a median total risk value of 4.6 (IQR 3.5-5.5). 94% of the patients with a total risk value ≦6.0 had not progressed to RA and RA development was observed in 83% of patients with a score >6. All patients with a score ≧8.0 had progressed to RA and 78% of patients with a score <8 did not develop RA. The AUC of the validation cohort was 0.97 (SE 0.024).

As current evidence on treatment of RA is based on large trials using patients fulfilling the 1987 ACR criteria for RA, fulfillment of these criteria was used as outcome. Alternative outcome measurements such as disease persistence or remission can be considered. Nevertheless, the use of fulfillment of the ACR criteria as outcome may lead to circularity as the items of the ACR-criteria are expected to result as predictive variables. However, several studies have shown that the ACR criteria themselves have low discriminative value in patients with UA and only a portion of the variables of the present prediction rule are items included in the ACR criteria. In the end it will most likely not make a large difference whether the outcome of a prediction rule is the diagnosis RA or disease persistence, as the ACR criteria are formulated based on RA patients with longstanding/persistent disease (mean disease duration 8 years) and the reported remission rate in these patients is low: 10-15%.

Misclassification may have occurred when patients who presented with UA were treated with any drug that has hampered the progression to RA. In case of misclassification, patients that would normally have progressed to RA would now be classified as non-RA. Exclusion of these misclassified patients, with supposedly high total risk values as they would be prone to develop RA, would result in an increased discriminative ability of the current prediction rule.

In certain embodiments, the positive and negative predictive values of the total risk value depend on the chosen cut-off levels. If the upper and lower cut-off values were 8.0 and 6.0, the corresponding positive predictive value and negative predictive value were respectively 84% and 91%. In the original cohort 25% of patients had a total risk value between 6.0 and 8.0; these patients had an equal chance to develop RA or not. In the validation cohort, the total risk value discriminated even better: a hundred percent of patients with a total risk value of 8.0 or higher had progressed to RA and 94% of patients with a total risk value of 6.0 or lower did not develop RA.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

REFERENCES

Each of the following references is incorporated by reference in their entireties for all purposes.

1. Lossos I S, Czerwinski D K, Alizadeh A A, et al. Prediction of survival in diffuse large-B-cell lymphoma based on the expression of six genes. N Engl J Med. 2004; 350 (18): 1828-37.
2. Hasenclever D, Diehl V. A prognostic score for advanced Hodgkin's disease. International Prognostic Factors Project on Advanced Hodgkin's Disease. N Engl J. Med. 1998; 339 (21):1506-14.
3. Lard L R, Visser H, Speyer I, et al. Early versus delayed treatment in patients with recent-onset rheumatoid arthritis: comparison of two cohorts who received different treatment strategies. Am J Med. 2001; 111 (6):446-51.
4. Goekoop-Ruiterman Y P, De Vries-Bouwstra J K, Allaart C F et al. Clinical and radiographic outcomes of four different treatment strategies in patients with early rheumatoid arthritis (the BeSt study): A randomized, controlled trial. Arthritis Rheum 2005; (11):3381-90.
5. Nell V, Machold K P, Eberl G, Stramm T A, Uffman M, Smolen J S. Benefit of very early referral and very early therapy with disease-modifying antirheumatic drugs in patients with early rheumatoid arthritis. Rheumatology (oxford) 2004; 43:906-14.
6. van Aken J, Van Dongen H, le Cessie S, Allaart C F, Breedveld F C, Huizing a T W. Long-term outcome of rheumatoid arthritis that presented with undifferentiated arthritis compared to rheumatoid arthritis at presentation—an observational cohort study. Ann Rheum Dis. 2006; 65 (1):20-5.
7. Tunn E J, Bacon P A. Differentiating persistent from self-limiting symmetrical synovitis in an early arthritis clinic. Br J Rheumatol. 1993; 32 (2):97-103.
8. Harrison B J, Symmons D P, Brennan P, Barrett E M, Silman A J. Natural remission in inflammatory polyarthritis: issues of definition and prediction. Br J Rheumatol. 1996; 35 (11):1096-100.
9. van Dongen H, van Aken J, Lard L R, et al. Treatment of Patients with Undifferentiated Arthritis with Methotrexate: a Double-Blind, Placebo-Controlled, Randomized Clinical Trial to Prevent Evolvement into RA. ACR 2005, abstract (479)L4.
10. Machold K P, Stamm T A, Eberl G J, et al. Very recent onset arthritis-clinical, laboratory, and radiological findings during the first year of disease. J. Rheumatol. 2002; 29 (11):2278-87.

11. van Aken J, van Bilsen J H, Allaart C F, Huizinga T W, Breedveld F C. The Leiden Early Arthritis Clinic. Clin Exp Rheumatol. 2003; 21 (5 Suppl 31):S100-5.
12. Hazes J M, Hayton R, Silman A J. A re-evaluation of the symptom morning stiffness. J Rheumatol 1993; 20:1138-42.
13. Vliet Vlieland Th P, Zwinderman A H, Breedveld F C, Hazes J M. Measurement of morning stiffness in rheumatoid arthritis clinical trials. J Clin Epidemiol 1997; 50:757-63.
14. Van Riel P L, van Gestel A M, Scott D G. In EULAR handbook of clinical assessments in rheumatoid arthritis. Alphen aan den Rijn, The Netherlands: Van Zuiden Communications; 2000, 10-11.
15. Van der Heijde D M. Plain X-rays in rheumatoid arthritis: overview of scoring methods, their reliability and applicability. Baillieres Clin Rheumatol. 1996; 10:435-53.
16. Harrell F E, Lee K L, Mark D B. Multivariate prognostic models, evaluating assumptions and accuracy, and measuring and reducing errors. Stat Med. 1996; 15:361-87.
17. Visser H, le Cessie S, Vos K, Breedveld F C, Hazes J M. How to diagnose rheumatoid arthritis early: a prediction model for persistent (erosive) arthritis. Arthritis Rheum. 2002; 46 (2):357-65.
18. Harrison B J, Symmons D P, Barrett E M, Silman A J. The performance of the 1987 ARA classification criteria for rheumatoid arthritis in a population based cohort of patients with early inflammatory polyarthritis. American Rheumatism Association. J Rheumatol. 1998; 25 (12):2324-30.
19. Harrison B, Symmons D. Early inflammatory polyarthritis: results from the Norfolk Arthritis Register with a review of the literature. II. Outcome at three years. Rheumatology (Oxford). 2000; 39 (9):939-49.
20. Symmons D P, Hazes J M, Silman A J. Cases of early inflammatory polyarthritis should not be classified as having rheumatoid arthritis J. Rheumatol. 2003; 30 (5):902-4.
21. Green M, Marzo-Ortega H, McGonagle D, et al. Persistence of mild, early inflammatory arthritis: The importance of disease duration, rheumatoid factor, and the shared epitope. Arthritis Rheum. 1999; 42:2184-88.
22. Linn-Rasker S P, Allaart C F, Kloppenburg M, Breedveld F C, Huizinga T W J. Sustained remission in a cohort of patients with RA: association with absence of IgM-rheumatoid factor and absence of anti-CCP antibodies. Int J Advances Rheumatology. 2004; 2 (4):4-6.
23. van der Helm-van Mil A H, Dieude P, Schonkeren J J, Cornelis F, Huizinga T W. No association between tumour necrosis factor receptor type 2 gene polymorphism and rheumatoid arthritis severity: a comparison of the extremes of phenotypes. Rheumatology (Oxford). 2004; 43 (10): 1232-4.
24. Aletaha D, Breedveld F C, Smolen J S. The need for new classification criteria for rheumatoid arthritis. Arthritis Rheum. 2005:52:3333-36.
25. Visser H. Early diagnosis of rheumatoid arthritis. Best Practice & Research Clinical Rheumatology. 2005:19 (1): 55-72.
26. Morel J, Combe B. How to predict prognosis in early rheumatoid arthritis. Best Practice & Research Clinical Rheumatology. 2005:19 (1):137-46.

The invention claimed is:

1. A method of predicting whether an individual with undifferentiated arthritis will develop rheumatoid arthritis, wherein the method comprises the steps of:

determining in a blood or blood fraction sample for the individual at least one first clinical parameter value selected from:
i) serum level of C-reactive protein, HS C-reactive protein (HS CRP) or erythrocyte sedimentation rate (ESR);
ii) presence or absence of Rheumatoid Factor autoantibodies or Rheumatoid Factor autoantibody titers; and
iii) presence/absence of anti-CCP antibodies or anti-CCP antibody titers;

determining for the individual at least one second clinical parameter value selected from: age of the patient, gender of the patient, localization of joint complaints, severity of VAS morning stiffness, number of tender joints, and number of swollen joints;

assigning a risk value for each first and second clinical parameter value, and calculating a prediction score to thereby predict whether the individual will develop rheumatoid arthritis.

2. The method of claim 1, wherein at least two first clinical parameters are determined.

3. The method of claim 1, wherein all second clinical parameter values are determined.

4. A method according to claim 1, wherein all three first clinical parameter values are determined.

5. The method according to claim 1, wherein the prediction score is calculated as a sum of the risk values for the first and second clinical parameter values.

6. The method according to claim 5, wherein the risk values assigned to respective parameter values are between 50% and 150% of the risk values in a)-i):
a) a risk value of 0 for less than 5 mg/L C-reactive protein; a risk value of 0.6 for 5-50 mg/L C-reactive protein; a risk value of 1.6 for more than 50 mg/L C-reactive protein;
b) a risk value of 0 for the absence of the Rheumatoid factor; a risk value of 0.8 for the presence of the Rheumatoid factor;
c) a risk value of 0 for the absence of anti-CCP antibodies; a risk value of 2.1 for the presence of anti-CCP antibodies;
d) a risk value of 0.02 for each year of age;
e) a risk value of 0 for male gender; a risk value of 0.8 for female gender;
f) a risk value of 0.6 in case of involvement of small joints hands and feet; a risk value of 0.5 in case of symmetric involvement; a risk value of 0.8 in case of involvement of upper extremities; or a risk value of 1.3 in case upper and lower extremities;
g) a risk value of 0 for a length of the VAS morning stiffness less than 26 mm; a risk value of 1 for a length of the VAS morning stiffness of 26-90 mm; a risk value of 2.2 for a length of the VAS morning stiffness more than 90 mm;
h) a risk value of 0.6 for 4-10 tender joints; a risk value of 1.2 for more than 10 tender joints; and,
i) a risk value of 0.4 for 4-10 swollen joints; a risk value of 1 for more than 10 swollen joints; and
whereby the maximum prediction score is 14 for an age of 100 years.

7. The method according to claim 6, wherein the risk values assigned to respective parameter values are between 75% and 125% of the risk values in a)-i):
a) a risk value of 0 for less than 5 mg/L C-reactive protein; a risk value of 0.5 for 5-50 mg/L C-reactive protein; a risk value of 1.5 for more than 50 mg/L C-reactive protein;

b) a risk value of 0 for the absence of the Rheumatoid factor; a risk value of 1 for the presence of the Rheumatoid factor;
c) a risk value of 0 for the absence of anti-CCP antibodies; a risk value of 2 for the presence of anti-CCP antibodies;
d) a risk value of 0.02 for each year of age;
e) a risk value of 0 for male gender; a risk value of 1 for female gender;
f) a risk value of 0.5 in case of involvement of small joints hands and feet; a risk value of 0.5 in case of symmetric involvement; a risk value of 1 in case of involvement of upper extremities; or a risk value of 1.5 in case upper and lower extremities;
g) a risk value of 0 for a length of the VAS morning stiffness less than 26 mm; a risk value of 1 for a length of the VAS morning stiffness of 26-90 mm; a risk value of 2 for a length of the VAS morning stiffness more than 90 mm;
h) a risk value of 0.5 for 4-10 tender joints; a risk value of 1 for more than 10 tender joints; and,
i) a risk value of 0.5 for 4-10 swollen joints; a risk value of 1 for more than 10 swollen joints.

8. The method according to claim 6 or 7, wherein the risk for the individual for developing rheumatoid arthritis is determined by correlating the prediction score for the individual with the risk associated with that prediction score in accordance with a probability distribution.

9. The method according to claim 1, wherein the undifferentiated arthritis is recent onset undifferentiated arthritis.

10. A system for determining a risk of an individual with undifferentiated arthritis for developing rheumatoid arthritis, the system comprising:
a) a sample analyzer configured to determine in a blood or blood fraction sample a set of clinical parameters comprising:
(i) serum level of C-reactive protein (CRP), HS-C-reactive protein (HS-CRP) or erythrocyte sedimentation rate (ESR);
(ii) presence or absence of Rheumatoid factor autoantibodies or Rheumatoid factor autoantibody titers; and
(iii) presence or absence of anti-CCP antibodies or anti-CCP antibody titers; and
b) a computing device configured to assign a risk value to each clinical parameter, wherein the computing device accesses data stored in a memory associating ranges of values for each of the clinical parameters with respective risk values, the computing device further configured to determine a risk that the individual will develop rheumatoid arthritis based at least partly on the assigned risk values.

11. The system of claim 10, wherein the sample analyzer is located remote from the computing device.

12. The system of claim 11, wherein the clinical parameters are transmitted to the computing device via a network communication link.

13. The system of claim 10, wherein the sample analyzer is located proximate the computing device.

14. The system of claim 10, wherein the computing device is further configured to transmit one or more electronic messages indicating the determined risk.

15. The system of claim 10, wherein the computing device receives the clinical parameters via a web interface in data communication with the computing device.

16. The system of claim 10, wherein the computing device is further configured to assign a risk value to at least one of patient age; patient gender; a localization of joint complaints; a length of a VAS morning stiffness; a number of tender joints; and a number of swollen joints.

17. A method for determining a risk that an individual with undifferentiated arthritis will develop rheumatoid arthritis, wherein the method comprises the steps of:
determining in a blood or blood fraction sample for the individual a set of first clinical parameter values comprising:
serum level of C-reactive protein, HS C-reactive protein (HS CRP) or erythrocyte sedimentation rate (ESR);
presence or absence of Rheumatoid factor autoantibodies or Rheumatoid Factor autoantibody titers; and
presence/absence of anti-CCP antibodies or anti-CCP antibody titers;
determining for the individual a set of second clinical parameter values comprising at least two of: patient age, patient gender, localization of joint complaints, severity of VAS morning stiffness, number of tender joints, and number of swollen joints;
assigning a relative risk value for each first and second clinical parameter value, wherein the risk values are:
a) a risk value of about 0 for less than 5 mg/L C-reactive protein; a risk value of about 0.6 for 5-50 mg/L C-reactive protein; a risk value of about 1.6 for more than 50 mg/L C-reactive protein;
b) a risk value of about 0 for the absence of the Rheumatoid factor; a risk value of about 0.8 for the presence of the Rheumatoid factor;
c) a risk value about 0 for the absence of anti-CCP antibodies; a risk value of about 2.1 for the presence of anti-CCP antibodies;
d) a risk value of about 0.02 for each year of age;
e) a risk value of about 0 for male gender; a risk value of about 0.8 for female gender;
f) a risk value of about 0.6 in case of involvement of small joints hands and feet; a risk value of about 0.5 in case of symmetric involvement; a risk value of about 0.8 in case of involvement of upper extremities; or a risk value of about 1.3 in case upper and lower extremities;
g) a risk value of about 0 for a length of the VAS morning stiffness less than 26 mm; a risk value of about 1 for a length of the VAS morning stiffness of 26-90 mm; a risk value of about 2.2 for a length of the VAS morning stiffness more than 90 mm;
h) a risk value of about 0.6 for 4-10 tender joints; a risk value of about 1.2 for more than 10 tender joints; and,
i) a risk value of about 0.4 for 4-10 swollen joints; a risk value of about 1 for more than 10 swollen joints;
calculating the sum of the risk values to determine a prediction score; and
correlating the prediction score to a risk for developing rheumatoid arthritis.

\* \* \* \* \*